United States Patent [19]

Garwin et al.

[11] Patent Number: 4,595,990
[45] Date of Patent: Jun. 17, 1986

[54] EYE CONTROLLED INFORMATION TRANSFER

[75] Inventors: Richard L. Garwin, Scarsdale; James L. Levine, Yorktown Heights, both of N.Y.

[73] Assignee: International Business Machines Corporation, Armonk, N.Y.

[21] Appl. No.: 480,992

[22] Filed: Mar. 31, 1983

Related U.S. Application Data

[63] Continuation of Ser. No. 221,660, Dec. 31, 1980, abandoned.

[51] Int. Cl.[4] ............... G06F 15/40; G06F 15/626
[52] U.S. Cl. ........................... 364/518; 340/365 P; 364/709
[58] Field of Search ............ 364/518, 525, 709; 358/93, 107, 113; 340/365 P; 356/152; 351/209; 250/203 CT, 209, 215, 216, 221, 349

[56] References Cited

U.S. PATENT DOCUMENTS

| | | | |
|---|---|---|---|
| 3,379,885 | 4/1968 | Nork | 250/221 X |
| 3,507,988 | 4/1970 | Holmes | 178/6.8 |
| 3,678,283 | 7/1972 | La Baw | 250/216 |
| 3,895,860 | 7/1975 | Townsley | 351/39 |
| 3,986,030 | 10/1976 | Teltscher | 250/349 |
| 4,034,401 | 4/1976 | Mann | 358/93 |
| 4,059,348 | 11/1977 | Jernigan | 351/209 X |
| 4,102,564 | 7/1978 | Michael | 351/209 X |
| 4,109,145 | 8/1978 | Graf | 250/221 X |
| 4,209,255 | 6/1980 | Heynau et al. | 358/93 X |

FOREIGN PATENT DOCUMENTS 7706532 2/1977 France .
1581018 12/1980 United Kingdom .

OTHER PUBLICATIONS

Merchant et al., "Remote Measurement of Eye Direction Allowing Subject Motion Over One Cubic Foot of Space *IEEE Trans. on Biomedical Engineering,* vol. BME-21 #Jul. 1974, pp. 309-317.
Journal of Optical Society, 63, No. 8, Aug. 1973, pp. 921 to 928.
IEEE Transactions on Biomedical Engineering, vol. BME21, No. 4, Jul. 1974.
NASA Report, CR-1422, Oct. 1969.
Text-Vision and Visual Perception, Wiley, 1965, pp. 49-51.
Psychological Bulletin, 85, 1978, pp. 615-660.
Biological Psychology Bulletin, vol. 3, 1974, pp. 99-108.

*Primary Examiner*—James D. Thomas
*Assistant Examiner*—Dale M. Shaw
*Attorney, Agent, or Firm*—Alvin J. Riddles

[57] ABSTRACT

Information is transferred interactively between a user and an information processor by establishing the direction of the user's gaze or visual focus with relation to portions of a viewing surface and thereafter the direction of the user's gaze or visual focus to a specific portion of the viewing surface conveys information. The direction of a user's gaze is established through a reflected signal from the operator's eyeball.

1 Claim, 15 Drawing Figures

EYE CONTROLLED INFORMATION TRANSFER

This is a continuation of application Ser. No. 221,660 filed Dec. 31, 1980, now abandoned.

DESCRITPION

1. Technical Field

The field of the invention is that of user-machine communication and specifically that of the interactive transfer of information to an information processor employing the direction of the operator's visual focus or gaze to enter information.

The human factor aspect of user-machine communication is receiving a great deal of attention. One of the more recent findings in the human factor studies is the fact that there are wide variations in individuals between intellectual perception and a response delivered through the individual's psychomotor capabilities. The goal in such communication is to provide flexibility that can overcome physical limitations of a user and permit communication with reduced training of the user.

2. Background Art

There has been effort in the art to develop communication using the muscles of the eyeball. The use of eye position information has been described in U.S. Pat. No. 3,507,988 in connection with broad area scanning to identify a specific portion of the broad area that is receiving attention from the operator. Eye motion has further been used to direct servomechanisms. Musical instrument and typewriter operation by a paraplegic is in U.S. Pat. No. 3,986,030. The position of focus of the eye has been used to aim aircraft armament as described in U.S. Pat. No. 4,034,401.

In the prior art applications of direction of vision information, the information signal has been used only to actuate a programmed servo-mechanism.

DESCRIPTION OF THE DRAWINGS

FIG. 6 comprising of FIGS. 6.1 and 6.2 is a functional logic diagram for processing the video data.

FIG. 11 comprising of FIGS. 11.1-11.3 is a flowchart for detecting information conveying eye movements.

DISCLOSURE OF THE INVENTION

The invention provides capability for interactive communication between a user and a responsive piece of apparatus, employing a vision direction indicator which communicates a series of user choices.

The invention involves establishing several discrete information input locations such as by partitioning the viewing area, determining the aiming point of the direction of gaze of the user on a particular point and then constructing an interactive communication by assembling iterative instances of point of gaze on individual discrete information input locations and feedback to the user. The feedback, for example, may be visual, auditory or tactile.

The preferred embodiment employs light reflected from the eyeball of a user to establish direction of gaze and employs parts of a partitioned display area as the individual discrete information input locations. The equipment that determines direction of gaze includes means to distinguish an information communicating series of eye movements for the eyes of a particular user from that of involuntary eye movements, noise in the system, and the usual back-and-forth eye movements associated with reading and information identification.

A series of instances of the gaze being directed to particular discrete information input locations is employed to formulate a decision assumption and then the act of verification of the decision assumption is assembled as an interactive information transfer increment.

In accordance with the invention, the direction of a user's gaze is employed to determine what portion of a quantity of information in the field of vision is receiving attention as a selection over other portions. Optical direction detection apparatus in conjunction with an information processor is capable of distinguishing selection eye movements from other eye behavior peculiar to the user and from unwanted eye movements. For simplicity, the aiming point in the field of view of the user will be referred to hereafter as direction of gaze. The information processor should be able to process direction of gaze information in a period of time that is short with respect to the individual physical eye movement so that a number of eye direction readings can take place during the usual time required for eye movement. The digital computer, because of its speed of response, makes an excellent object for the storage of information and the information processing required for the removal of extraneous eye movement information.

In the light of the principles set forth in connection with the preferred embodiment of a gaze direction indicator using a light reflected from the eyeball in combination with a digital computer processor, it will be apparent to one skilled in the art that so long as the information processed and the rapidity of processing are adequate, the benefits of the invention will be achieved by many types of apparatus.

It is essential only, in order to achieve the high level of communication of the invention, that apparatus be provided, that will establish the direction of gaze with respect to a plurality of locations in the field of view of the user many times during the time of eye movement of a typical user.

Figure 1:
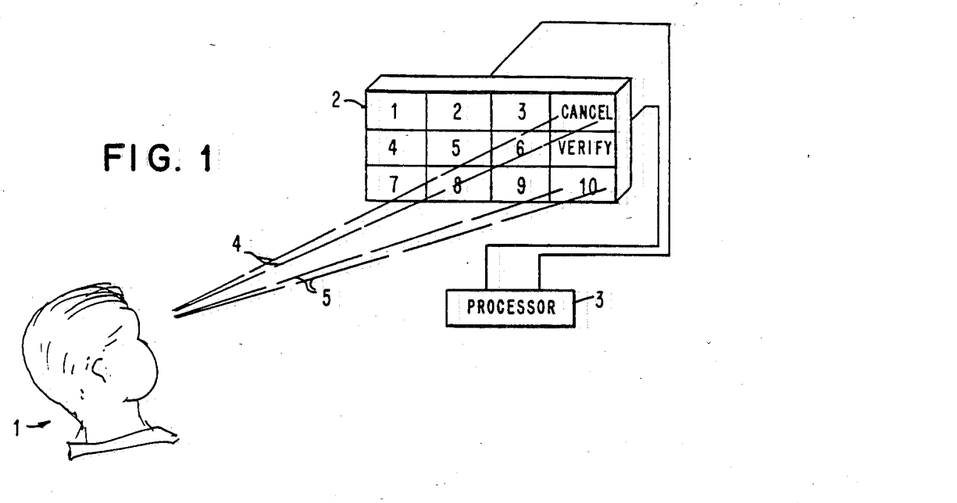
FIG. 1 is an illustration of a user viewing a partitioned display.

Referring to FIG. 1, a user 1 is shown viewing a display 2 which is connected to a processor 3 which may, for example, be a digital computer. The viewing area of the display is partitioned in such a way that different information is displayed in discrete areas shown as separated by lines, and the different directions of the gaze 4 and 5 of the user are employed to communicate to the processor 3 which, and in what order of a plurality of items displayed at 2, were selected.

It is necessary that the means for determining the direction of gaze be capable of distinguishing useful information from other information caused by undesirable eye movements and noise that could limit effectiveness.

BEST MODE FOR CARRYING OUT THE INVENTION

It is necessary to briefly review certain features of the human visual system in order to understand the functions of the various parts which make up this invention. The human vision system appears to provide a uniformly clear and sharp view of the world. This is in fact an illusion provided by the brain and a portion of the nervous system lying between the eye and brain. It is well known that the human eye can see clearly only in a narrow region about 1 degree wide, located a few degrees from the optic axis of the eyeball. This results from an uneven distribution of photo-receptors in the retina, and from optical abberations. In viewing a wide field, the eyeball is moved in rapid jumps lasting a few milliseconds (ms), followed by fixations lasting approximately 200 ms. Clear vision only occurs during such fixations.

Because of the relatively long time required for nerve impulses to travel between the brain and the muscles which move the eyeball, most eye movements are normally controlled by a quasi-independent portion of the nervous system located close to the eyes. The brain usually provides only general directions to this system, hence most eye movements are only partially voluntary. Nevertheless, most humans are able to direct the eyes fairly steadily at an object for extended periods of time, for example, longer than 0.3 seconds, and with considerable accuracy, for example, 0.5 degrees. A number of devices can determine the orientation of an eyeball with good accuracy, on a time scale adequate to follow the detailed eye movements. Such a device can be used to develop a control signal based on a subject's voluntary eye movements. These signals can then be used to initiate various actions based on the specific direction of gaze. As an example, a subject could request display of a page of text from a displayed table of contents.

There are several difficulties in putting such ideas into practice that have been surmounted in accordance with the invention. The major difficulty is in separating the eye movements intended for control from those which are involuntary. A second difficulty is in dealing with noise and other instrumental errors arising from the device used for tracking the eye movements. A third difficulty is in providing a flexible means of control capable of dealing with a wide variety of possible tasks. A fourth difficulty is in dealing with mistakes made by the user, including incorrect eye movements and mistakes of intent.

These problems in accordance with the preferred embodiment, are conveniently dealt with by transmitting the signals from the eyetracking device to a digital computer equipped with suitable interface and programs.

While the term "user" is considered to be a human in most interactive communication applications, it will be recognized by one skilled in the art that in certain interactive applications, an animal could be involved.

The preferred form of the present invention consists of the combination of a reflected light eyetracking device involving both analog and digital computer processing, a set of carefully designed programs which deal with the above-described difficulties, and a computer controlled display screen, for example, a cathode ray tube (CRT) for presenting choices for eye selection. The invention is not limited to such a combination, as the basic features could be provided by digital or analog circuitry designed for a specific task and which embody the principles incorporated in the programs. Similarly, many types of display surfaces are possible. An example would be a message board with indicator lamps. However, the preferred combination is particularly convenient and can be programmed to provide a very wide variety of eyecontrolled functions.

EYETRACKING DEVICE

The preferred eyetracking device is similar to one published by John Merchant in IEEE Transactions in Biomedical Engineering, BME 21, No. 4, July 1974. Its operating principles allow reasonably accurate measurements without unduly interfering with the subject's freedom of motion. However, the output signal from such a device and any others capable of overcoming the above-described difficulties will require more complex signal and data processing operations than has heretofore appeared in the art, in order to obtain an accurate and reliable indication of eyeball orientation. The device will first be described in order to be able subsequently to discuss the processing.

Figure 2:
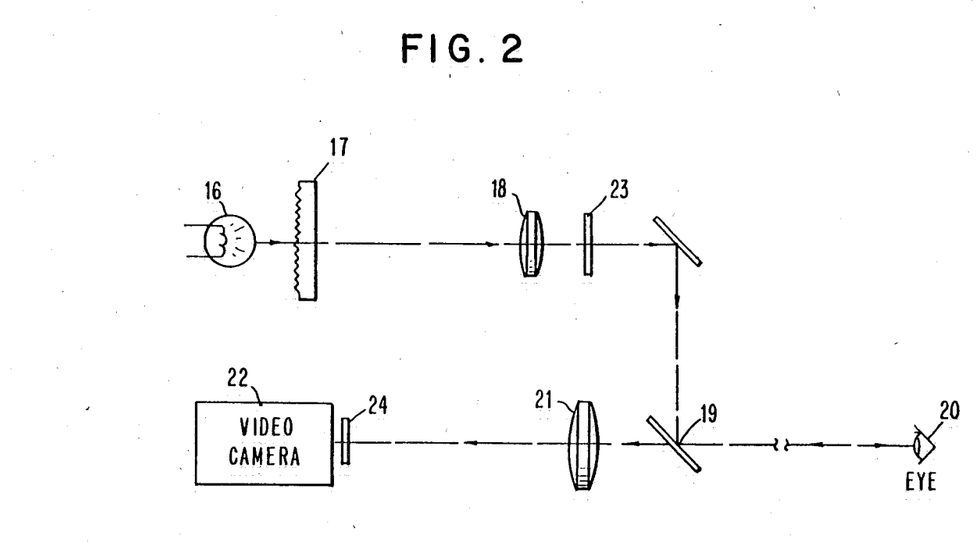
FIG. 2 is a detailed sketch of the light pattern of the eyetracking device used in measuring the direction of visual focus or gaze of the eyeball.

The eyetracking device of the Merchant type is an optical-electrical device whch is shown schematically in FIG. 2. Light from filament 16 is focused by lenses 17 and 18 chosen to focus the light onto half-silvered mirror 19 and to produce uniform illumination to the eye 20.

Some of this light is reflected back from the eye, passes through half-silvered mirror 19 and is collected by lens 21 to be imaged onto the faceplate of the vidicon tube in video camera 22. Infrared filter 23 removes most of the visible light so as not to disturb the subject represented by eye 20, while similar filter 24 blocks ambient light from the vidicon tube 22. The vidicon 22 is a commercial unit providing enhanced operation in the near infrared.

Figure 3:
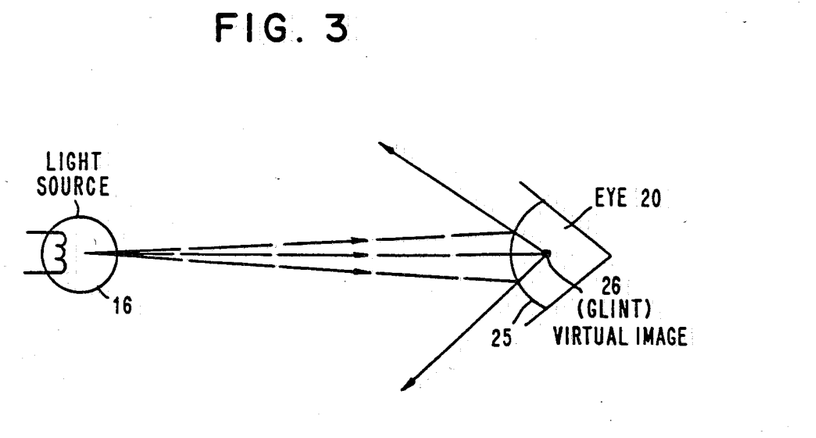
FIG. 3 is a diagram illustrating the light pattern when light strikes the eyeball.

The light reflected from the eye has two major components. The first component is the light reflected from the spherical front surface or cornea of the eye. It appears to originate in a small and very bright virtual image of the filament called the "glint". The formation of this corneal "glint" is shown in FIG. 3. The eye 20 is nearly spherical at the surface 25, so that this image remains nearly stationary as the eyeball rotates. The second component consists of light which has entered the eye 20 and been diffusely reflected from the retina. This light, not shown in FIG. 3, serves to illuminate the pupil of the eye from behind, forming a bright disk on the vidicon tube 22 of FIG. 2. The image is bright because the eye-lens directs this light back through the optical system with considerable efficiency. Unlike the "glint" 26, the pupil moves as the eye rotates. It will then be evident that the orientation of the eyeball can be inferred from the differential motion of the pupil center relative to the glint.

INTERFACE

Figure 4:
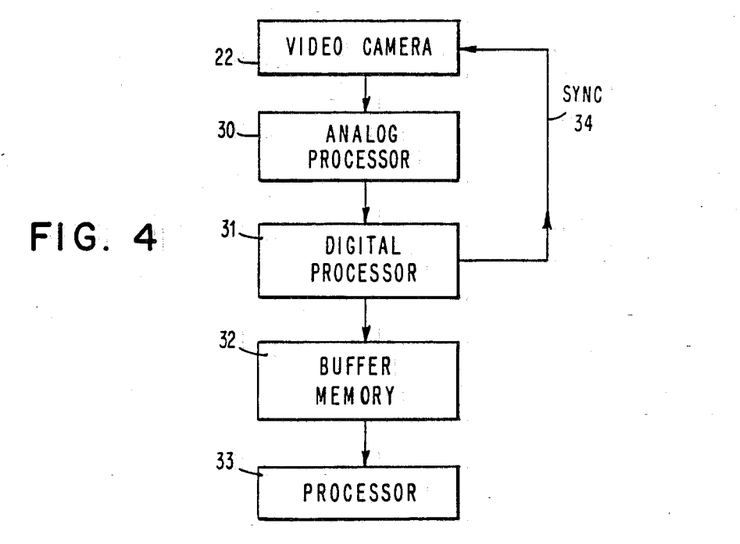
FIG. 4 is a diagram of a video signal preprocessor or interface.

The video signal from the camera 22 is processed in FIG. 4 in an electronic circuit containing analog 30 and digital 31 circuitry. This and a buffer 32 form an interface between the camera 20 and the digital computer 33.

In principle, the entire video image could be digitized and transferred to the computer for analysis. This is a present limitation because of the very large amount of information which would have to be handled in the short time available. Thus, a first function of the interface is to abstract only the relevant features from the video signal. These are the boundaries of the pupil disk outline and glint. A second function of the interface is to eliminate certain artifacts from the signal, including electrical and optical noise which occur too rapidly and/or frequently to be dealt with by the computer. The amount of light reaching the retina of the eye varies widely between different subjects. For a given subject there will also be pupil expansion and contraction. A third function of the interface is to minimize the effects of the resulting changes in signal strength. A fourth function is to buffer the flow of data so that new data can be collected while old data is being transferred to the computer and processed. In the following description, the circuits are described only functionally, as there are many well-known techniques for implementing any of them.

Figure 5:
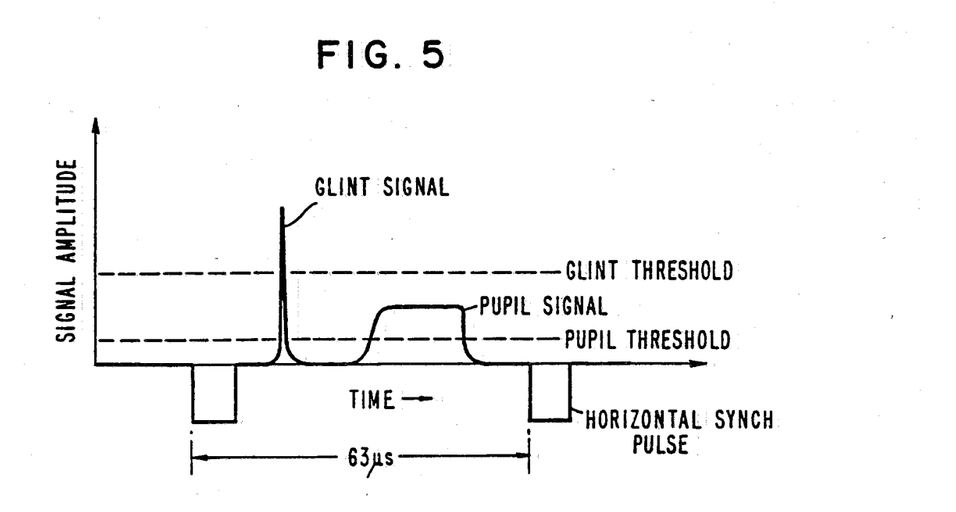
FIG. 5 is a diagram illustrating the relative signal magnitudes processed by a video tube in the apparatus of FIG. 2.

It will be appreciated by those skilled in the art that a video camera operates in a raster scanning mode in which the image is converted to an electrical signal line by line. Approximately 250 lines comprise a field, and are scanned in 16 ms. FIG. 5 shows the video signal voltage which occurs during a raster line which crosses both the glint and the pupil. The signal consists of a relatively long pulse from the pupil and a shorter and larger pulse from the glint. The other pulses are injected by the camera circuitry for purposes of synchronization. The glint signal may occur on top of the pupil signal as well as on a scan line which does not cross the pupil, according to the orientation of the eyeball. All three cases must be accommodated. The boundaries of the pupil and glint are first detected by analog circuits in analog processor 30 which sense the voltage difference between the signal and two threshold voltages. Let the threshold voltage for the pupil be $V_{tp}$, and that for the glint be $V_{tg}$. These values cannot be fixed because the signal levels vary substantially according to the size of the subject's pupil which varies with time, and to some extent with the direction of gaze. Therefore, a feature of this invention is a circuit which sets the thresholds adaptively. This consists of a peak sampling circuit of conventional nature which determines the maximum pupil signal level occurring during a given scan, and uses it to set the threshold levels for the next scan. Such a circuit is provided with a filter, so that the peak value represents the pupil signal rather than the narrow glint signal. The height of the glint signal depends critically on the focus of the camera lens, and is thus not a reliable indicator of signal strength. A circuit for these functions is set forth as FIG. 6. A video amplifier 40 is provided which buffers the signal from the camera 22. The amplifier signal is smoothed by a filter 41 to suppress the glint and is connected to a peak-detecting circuit 42. The output from the peak detector is then connected to a sample-and-hold circuit 43. The peak detecting circuit 43 is reset by a timed pulse on line 44 at the start of each raster line and the peak value is transferred to the sample-and-hold circuit by a second pulse on line 45 at the end of each raster line. The output $V_{sh}$ of the sample-and-hold circuit 43, is connected in parallel to two operational amplifier circuits 46 and 47, the outputs of which are the pupil and glint threshold voltages, respectively, and have the form as set forth in Equations 1 and 2, respectively.

$$V_{tp} = V_p + K_p V_{sh} \qquad \text{Eq. 1}$$

$$V_{tg} + V_g + K_g V_{sh} \qquad \text{Eq. 2}$$

where $V_{tp}$ is the pupil threshold level and $V_{tg}$ is the glint threshold level. The adjustable offset voltages ($V_p$ and $V_g$) ensure that the thresholds do not fall into the noise for scan lines not crossing the pupil, while the adjustable scale factors ($K_p$ and $K_g$) are set so that the thresholds will be approximately half the relevant signal level under normal conditions. The circuit then functions without adjustment for many subjects.

The threshold levels are compared with the output from the video amplifier by two analog comparator circuits, 48 and 49, for pupil and glint, respectively. The output of 48 is provided as a logical signal which switches from "0" to "1" on line 50 when the signal crosses the pupil threshold voltage. Similarly, the similar output of 49 changes from "0" to "1" on line 51 when the signal crosses the glint threshold voltage.

It is important that the detection be reliable because of the intended use of the device. Therefore, a second stage of detection is provided. The logical outputs of the two detectors 48 and 49 are clocked through pupil and glint digital shift registers 52 and 53, respectively, having many, for example, 32 parallel outputs. At any instant of time, the register outputs thus represent a short past history of the detected glint and pupil signals. The outputs are then combined in logic circuits which are arranged to provide a pulse when a specific edge or feature being detected appears. Thus, the left edge of the pupil is detected as a string of "0"s followed by a string of "1's" in the pupil shift register, with the simultaneous absence of any "1's" in a portion of the shift register as associated with the glint. This latter condition is necessary, because the pupil threshold level is lower than the glint level and will be crossed when the glint occurs. A logic circuit 54 receives the edge-detection pulses for the four edges (left and right edge of pupil and glint). These are counted in 55 and the circuit develops a logical output which becomes "1" if and only if all four edges are detected exactly once during a scan. This output is used to reject multiple edges caused, for example, by an eyelash in front of the pupil.

The location of each edge is converted to a digital number in the digital processor 31 as follows. The interface contains a fast digital oscillator 56 which serves as the source of synchronizing pulses 34 of FIG. 4 for the video camera 22 after suitable frequency division through logic unit 57 on line 58. At the start of each scan line, a counter 59 is reset and then incremented by the oscillator. When an edge is detected, the value of the counter 59 is stored in one of four holding registers or latches 63, and serves as the X coordinate of the edge. A second counter called 60 is reset at the beginning of each complete field and is incremented at the start of each scan line. This value serves as the Y coordinate of the edge. At the end of each scan line the contents of the counter 60 and the values stored in the temporary registers are transferred to the buffer memory 32 of FIG. 4, if the output of the logic circuit 54 indicates that all four edges have been detected exactly once.

The buffer memory 32 of FIG. 4 and 61 consists of three independent sections identified as Memory 1, Memory 2 and Memory 3. At any time, new data flows into one section, for example, Memory 1 old data can be transferred from a second one, Memory 2, to the processor 33 and the third Memory 3 is available in case the first buffer Memory 1 fills up before the second Memory 2 is emptied. This arrangement ensures that the computer 33 can always capture the most recent field of data. Access to the memory sections is controlled by memory control logic micro-processor 62.

The procedure is as follows. At the end of a video field, the interface of FIG. 4 will transfer a set of digital numbers representing the coordinates of the pupil and glint boundaries to the computer 33. These numbers are processed by a first group of procedures which will be referred to as the eyetracking device programs. These programs, in combination, compute the spatial coordinates which define the subject's direction of gaze. They correct for certain instrumental errors and provide a degree of discrimination against noise and artifacts in the raw data.

The computed values are then passed to a second group of procedures or programs which detect voluntary eye fixations and provide the desired control functions.

EYETRACKING DEVICE PROGRAMS

The eyetracking device programs consist of two subroutines which are identified as "EYETRACK" and "AIMPOINT". They are shown as simplified flowcharts in FIGS. 7 and 8. The purpose of the eyetrack subroutine is to find the center of the pupil and glint in such a way as to eliminate or minimize the effects of any errors of measurement. The AIMPOINT subroutine uses the results of eyetrack to compute the direction of gaze. The separation into two routines is purely for convenience in programming.

A wide variety of algorithms can be applied to the raw data in order to screen out invalid data points. The amount and perfection of such screening is limited primarily by the computational speed of the particular computer. The techniques described provide good discrimination against noise and artifacts and yet allow the computer to keep up with the field rate (60 per second) of the camera.

Figure 7:
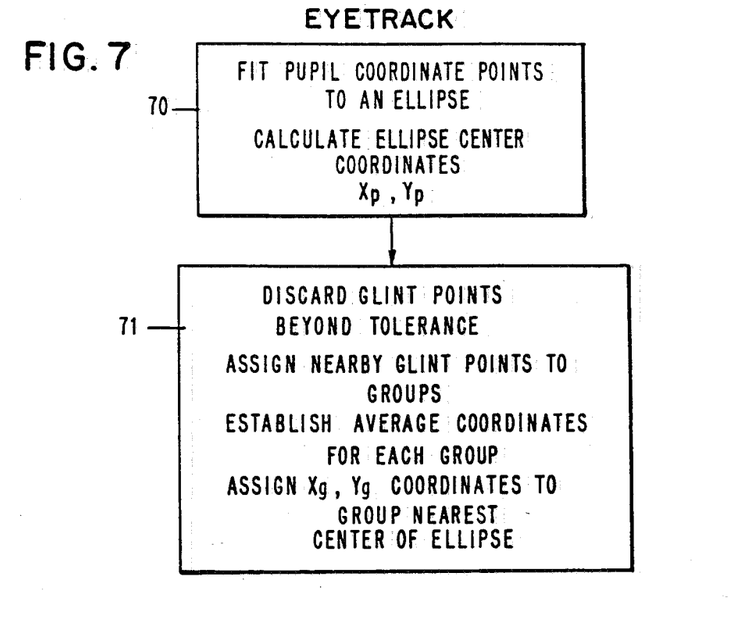
FIG. 7 is a flowchart for the eyetrack subroutine for tracking the axis of the eyeball.

In general, the camera will be located to one side of the user, there the circular pupil is viewed obliquely by the camera and thus appears to be an ellipse. The EYETRACK subroutine of FIG. 7 in section 70 finds the center of the pupil by fitting the previously digitized boundary points to the equation of a general ellipse. This method is particularly beneficial because it will work with only slightly reduced accuracy when a portion of the pupil is obscured by eyelids, eyelashes, etc. The general equation for an ellipse may be written as set forth in Equation 3.

$$AX^2 + 2GX + 2HXY + 2FY + BY^2 + 1 = 0 \qquad \text{Eq. 3}$$

The coefficients (A,G,H,F,B) are obtained by a least-squares mathematical technique which calculates the coefficients which minimize the errors between the actual data points and the curve represented by Equation 3. The coordinates $X_p$, $Y_p$ of the center of the pupil are then as set forth in Equations 4 and 5, respectively.

$$X_p = GB - FH/AB - H^2 \qquad \text{Eq. 4}$$

$$Y_p = FA - GH/AB - H^2 \qquad \text{Eq. 5}$$

With this procedure, noise reduction depends primarily on using a large number of data points, e.g., 30. A faster computer would allow a rejection of noisy data points by discarding those far from the computed curve represented by Equation 3. This would be followed by a second least squares fit to the remaining data points.

Figure 8:
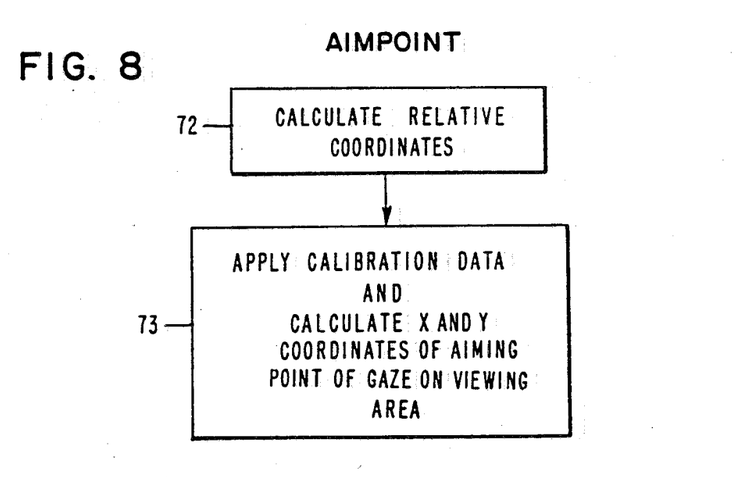
FIG. 8 is a flowchart for the aimpoint subroutine for establishing the aiming point of the direction of gaze.

Only a few glint points are normally obtained, hence more care is required to locate the center of the glint. The glint is treated in section 71 of EYETRACK subroutine as if it were a small, unresolved spot. The program first rejects glint points which are further from the computed pupil center than would be allowed by the geometry of the eye. This eliminates many artifacts, such as stray reflections from eyeglass frames and from the corners of the eye. It then associates nearby points into groups and finally selects the group closest to the pupil center as representing the true glint. The coordinates of this final group are averaged to find the glint coordinates $(X_g, Y_g)$. The subroutine provides an integer return code, "0" representing a successful computation. Various error conditions (e.g., no glint found) are represented by negative numbers. This code is used by the program which invoked the EYETRACK subroutine for control purposes. An example would be to retry the measurement or terminate if too many were invalid. The AIMPOINT subroutine of FIG. 8 takes the four numbers $(X_p, Y_p, X_g, Y_g)$ from the EYETRACK subroutine of FIG. 6 and computes the coordinates $(X_s, Y_s)$ of point on a display screen (or other surface) at which the eye is aimed. The exact formula for this computation is complex and requires evaluation of several trigonometric functions. This would require too many calculations for the present computer to do in the available time, hence a simplified numerical approximation in FIG. 8 is used. The relative coordinates $X_r = X_p - X_g$, $Y_r = Y_p - Y_g$ are calculated in section 72 as set forth in Equations 6 and 7, respectively.

$$X_s = C_1 + C_2 X_g + C_3 Y_g + C_4 X_r + C_5 Y_r + C_6 X_r Y_r + C_7 X_r^2 + C_8 Y_r^2 \qquad \text{Eq. 6}$$

$$Y_s = D_1 + D_2 X_g + D_3 Y_g + D_4 X_r + D_5 Y_r + D_6 X_r Y_r + D_7 X_r^2 + D_8 Y_r^2 \qquad \text{Eq. 7}$$

In the above, the constants $C_2, C_3, D_2, D_3$ represent the effect of moving the entire eye without rotation. They can be obtained conveniently as follows. A target is made consisting of a grid of small retroreflectors using reflective tape with known separation. This is placed in front of the optical system at the normal eye position and orientated so as to be parallel to the plane of the display surface. The spots then appear as glints whose coordinates, i.e., $X_g, Y_g$, can be found by using the EYETRACK subroutine. The constants $C_2, C_3, D_2, D_3$, can then be calculated from the change in $X_g$ and $Y_g$ versus known spot spacing which are equivalent to changes in $X_s$ and $Y_s$. The remaining coefficients represent the effect of rotating the eye. They depend on the internal details of a subject's eye, and must therefore be determined by a calibration procedure for each subject. The calibration data is used in FIG. 7, in section 73 and the XY coordinates of the gaze on the viewing area are calculated.

The approximation from Equations 6 and 7 is adequate for applications involving selection of targets separated in angle by a few degrees. Better accuracy can be achieved by a piecewise approximation. For example, several sets of coefficients for Equations 6 and 7 can be obtained for shall areas of the display surface as well as for the total surface. Then the latter can be used to select the smaller areas and a final calculation made.

CALIBRATION

Figure 9:
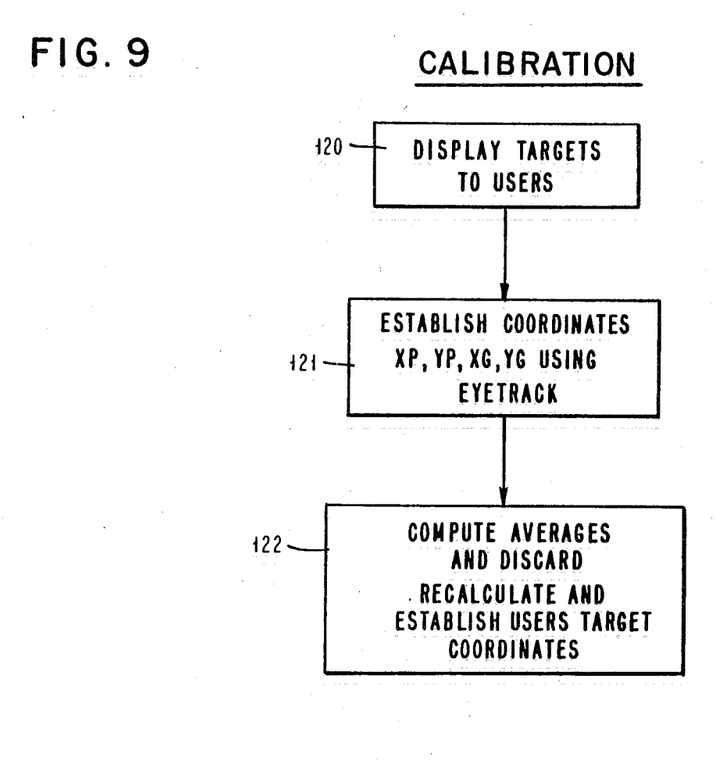
FIG. 9 is a flowchart for calibration.

A special program is provided for calibration. The flowchart is shown in FIG. 9. The program displays aiming marks on the display surface at known locations in section 120. The subject gazes steadily at each mark in turn. For each mark, the EYETRACK subroutine of FIG. 7 is invoked or called in section 121 a number of times and the coordinates stored in section 122. The average values of $X_p, Y_p, X_g, Y_g$ are calculated as set forth in Equations 4 and 5 for each calibration mark. The averaging is done in two steps. Preliminary averages are obtained using all the readings. Next, points far from the averages are discarded. Finally, the averages are recalculated using the remaining points. The computer reruns the calibration mark if too many points are rejected, or if the mean-square errors for the point are excessive. This provides excellent protection against errors which may occur if the subject blinks or inadvertently shifts his gaze while the data is being collected. After measurements have been made for all the marks, the coefficients $C_1$–$C_8$, $D_1$–$D_8$ of Equations 6 and 7 are obtained by a least squares fit of Equations 6 and 7 to the data, using the known target positions. The coefficients are stored on the computer disk along with the identity of the subject. The coefficients are used in section 51 of FIG. 7 in connection with the AIMPOINT subroutine of FIG. 7.

A special feature of the program is that some of the aiming marks are located at positions on the display surface having special meaning to the final control software such as to verify a decision. The apparent location of these points as seen by the subject are calculated from Equations 6 and 7 using the actual data values obtained during calibration. These values are also stored on the computer disk.

In general, the calibration constants are stable with time given for a given subject. However, occasional shifts do occur. In most cases, it is not necessary to do a complete recalibration. Instead, the constants $C_1$ and $D_1$ are adjusted using a subroutine called "CENTER". This subroutine displays a single target at a known location. It uses the EYETRACK and AIMPOINT subroutines of FIGS. 7 and 8, respectively, and the stored calibration constants from the calibration routine of FIG. 9 to determine the apparent location of the target as seen by the user, and then modifies the constants $C_1$ and $D_1$ so that the computed location agrees with the known location. Again, a number of measurements are taken and averaged, and screened for excess noise. In some cases, it is possible for a subject to use calibration constants obtained for a previous subject after such an adjustment. The accurate position of gaze information is now available to permit eye interactive control type of communication.

EYE-INTERACTIVE CONTROL

Figure 10:
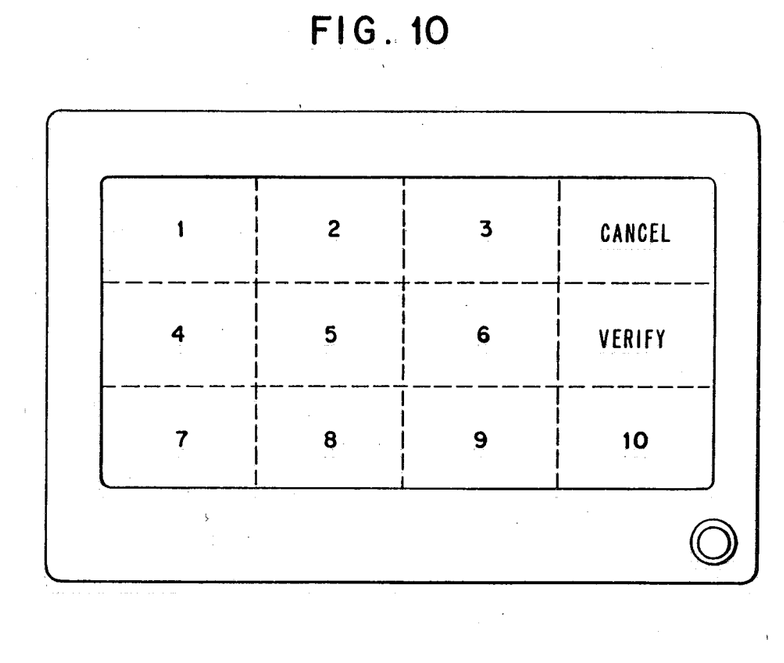
FIG. 10 is an illustration of a partitioned viewing area.

Eye-interactive control is based on the following general technique. The subject is presented with a number of targets having some meaning. For example, key words or phrases may be displayed A CRT or similar display is convenient, particularly if it is desired to change the targets frequently or interactively. In other situations, a static display including a sheet of paper may suffice. FIG. 10 illustrates the possible appearance of such a display, which contains 10 alternative choices plus two special locations identified by words VERIFY and CANCEL. The subject selects a particular target by directing his gaze at it in a way which is distinguishable from other eye-movements. These include fixations occurring while the subject studies the various targets or by random movements. The preferred selection method is for the subject to direct his eyes at the target for a time longer than the time normally required to read and comprehend a short word or phrase. Note that this time should be as short as possible in order to minimize system response time, and yet long enough to allow reading of the targets. A time of 0.3 seconds is suitable for many subjects. The first function provided by the control software is the detection of such a fixation in the presence of noise, other short fixations and various eye-movements.

The subject may inadvertently select an incorrect target, or the program may make an incorrect detection. Therefore, a second function is to indicate a detected target to the subject and then provide the subject with an opportunity to either confirm or reject that choice. The areas in FIG. 9 labelled VERIFY and CANCEL are used for this purpose. In cases such as those in which new choices are presented in response to a selection, the subject can "lose control" of the system without the above feature. A final function is to initiate the desired action according to the meaning assigned to the target. This may be virtually anything susceptible of control by a computer, including but not limited to, presentation of textual material, telephone dialing or control of a wheelchair or other vehicle to go left, right, faster or slower.

FIXATION DETECTION PROGRAM

The procedure for detecting a communicating fixation is contained in a program called DETECT and illustrated by the flowchart of FIG. 11 which, for simplicity, will be applied to the example layout shown in FIG. 10. This program uses the previously described subroutines EYETRACK and AIMPOINT to obtain repeated measurements of the direction of the gaze. Let the display surface be divided into cells which contain the various targets. For convenience, let the cells be numbered, say from 1 to N, such as 1 to 10 in FIG. 10. The cell locations can be defined by the coordinates of the cell centers, $X_c, Y_c$, plus or minus some tolerance in the X and Y directions. These can be stored in a list which may be changed according to the task. In many cases, some of the cells will be unused at various times. Therefore, it is convenient to store a second list denoting "active" cells. The cell locations $X_c, Y_c$ may be the true spatial coordinates of the cells on the display surface. A preferred method is to use the apparent cell locations obtained during the calibration procedure. These numbers are more reliable, as systematic errors in the calibration equations are then compensated.

After each measurement, the aiming coordinates, $X_s, Y_s$ obtained from the AIMPOINT subroutine are compared against the list, and a cell number associated if a match is found to an active cell within the tolerance range. A successful match may be considered as a "hit". Because the measurements are taken at regular intervals, in accordance with the invention, it suffices to count the number of hits in a given cell in order to recognize a long fixation. For example, at 60 measurements per second, 20 measurements require about 0.33 seconds which is long enough for typical subjects.

In order to provide some immunity against random noise, the program requires two consecutive hits in a cell before counting it. The variable PREVIOUS is used to hold the last cell number detected. This is initialized to a non-existent cell number, for example, −1, to deal with the first pass through the subroutine. Thereafter, each new reading is compared with PREVIOUS, and only counted if it agrees. The value of PREVIOUS is then updated with the new cell number. Further immunity can be obtained by requiring, for example, 3 or more consecutive hits on the same cell. Note that this is not equivalent to filtering, which can produce steady but erroneous readings should the eye flicker rapidly between two cells.

A flowchart for eye-movement comparison is provided in FIG. 11 wherein block-shaped sections represent procedures and diamond-shaped sections represent tests.

Referring to the flowchart of FIG. 11, the program starting at 80 operates in one of two modes as defined by the variable MODE. In the first mode of operation, MODE=1 SET IN 81, hits on the VERIFY and CANCEL cell are ignored and the program attempts to find a fixation on one of the cells 1 through 10 of FIG. 10. In the second mode of operation, MODE=2, beginning at section 82 labelled START 1, hits are only counted if they fall in the CANCEL or VERIFY cells as illustrated in FIG. 10. This mode of operation provides the user with confirm or reject capability.

In section 83 the counters are set. The EYETRACK and AIMPOINT subroutines and the cell number on which the aiming point of the gaze is specified in section 84. In section 85 when a cell number is equal to the previous value, it is assigned to the variable CURRCELL (current cell). Each time CURRCELL is again hit, the variable NCURR is incremented. If this exceeds a critical number N1 then a long fixation is assumed to have occurred. N1 defines the duration of the fixation. If a new cell is hit first, then this new cell number is stored as to the variable NEWCELL. Additional hits on this are counted by incrementing the variable NNEW. If this exceeds a critical number N2 before NCURR reaches N1, it is assumed that the eye has transferred attention away from the first cell and onto the new one. If this occurs, the value of CURRCELL is replaced by NEWCELL, the counting variable NCELL is replaced by NNEW, NNEW is reset to zero and the process continues. A value for N2 of about 6 which requires about 0.1 seconds, works well for many subjects.

It will be evident that the eye can shift from cell to cell, reading or studying the targets briefly until it finally stops for a relatively long time at the target of choice. Detection will then occur and the short intermediate fixations and other eye-movements will have been effectively ignored.

When detection of fixation as labelled on line 86 occurs, the subroutine shifts to MODE 2 in section 87 and provides visual feedback to the subject. This may consist of changing the intensity of the target word on a CRT display, of flashing an indicator lamp next to the target on a fixed indicator board, etc. The program then provides the subject with the desired opportunity to confirm or reject the selection. To do this, the program resumes EYETRACKING as before. However, only hits on the VERIFY and CANCEL cell are counted.

These are processed as before, although the critical value N1 can be lower because the subject soon learns where CANCEL and VERIFY are and has no need to read them. Because these are always present, they need not be on a changeable portion of the display but can be located to one side. If a fixation occurs on the CANCEL cell, this is taken to indicate a rejection by the subject. The feedback is removed and processing restarts in MODE 1 in section 80. If a fixation occurs first on the VERIFY cell, it is taken to indicate a satisfactory choice. Then the action associated with the selected cell is performed, indicated schematically in the flowchart as an invocation of an ACTION subroutine. In general, EYETRACKING will resume as before after the required action is complete.

Provision can be made for changing the values N1 and N2 which relate to the timing of fixations, as there is some variability among users. Optimum values are easily found by trial and error, starting from typical values. Secondly, an additional fixed target can be located far from the display surface. A gaze directed at this target inhibits further action until the user looks again at the target. This is very useful when the user needs time for thought or careful study of the display surface. Finally, a means can be provided for initiating a centering recalibration and for manually terminating operations.

Figure 12:
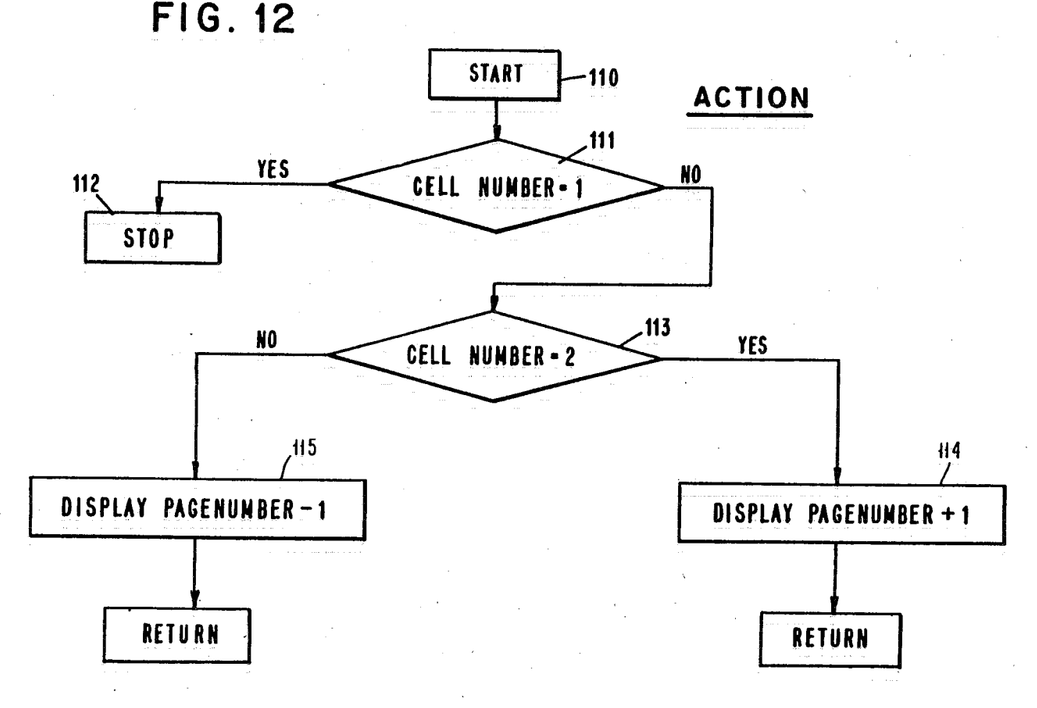
FIG. 12 is a flowchart for executing action on a communicated decision.
Figure 61:
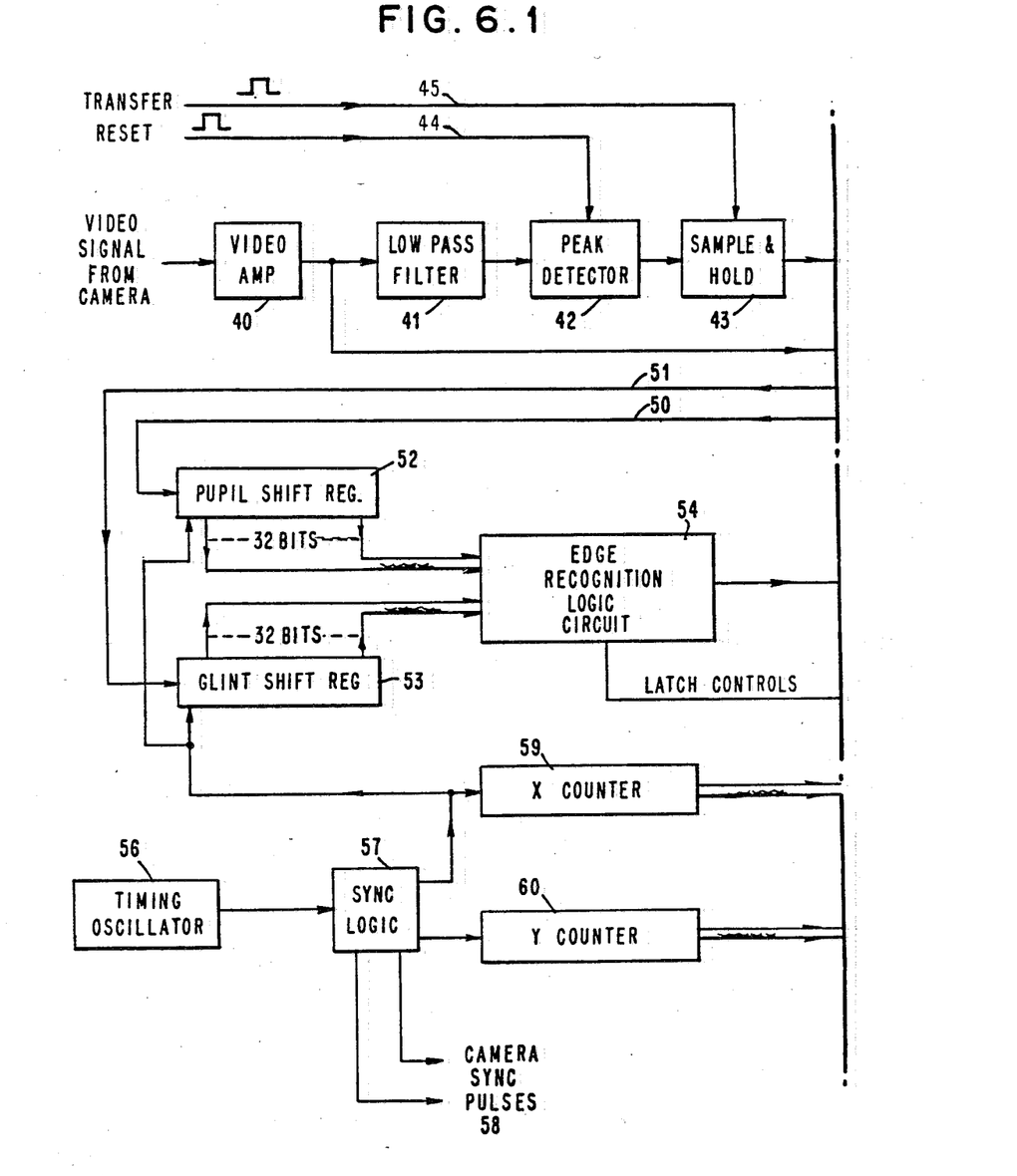
Figure 62:
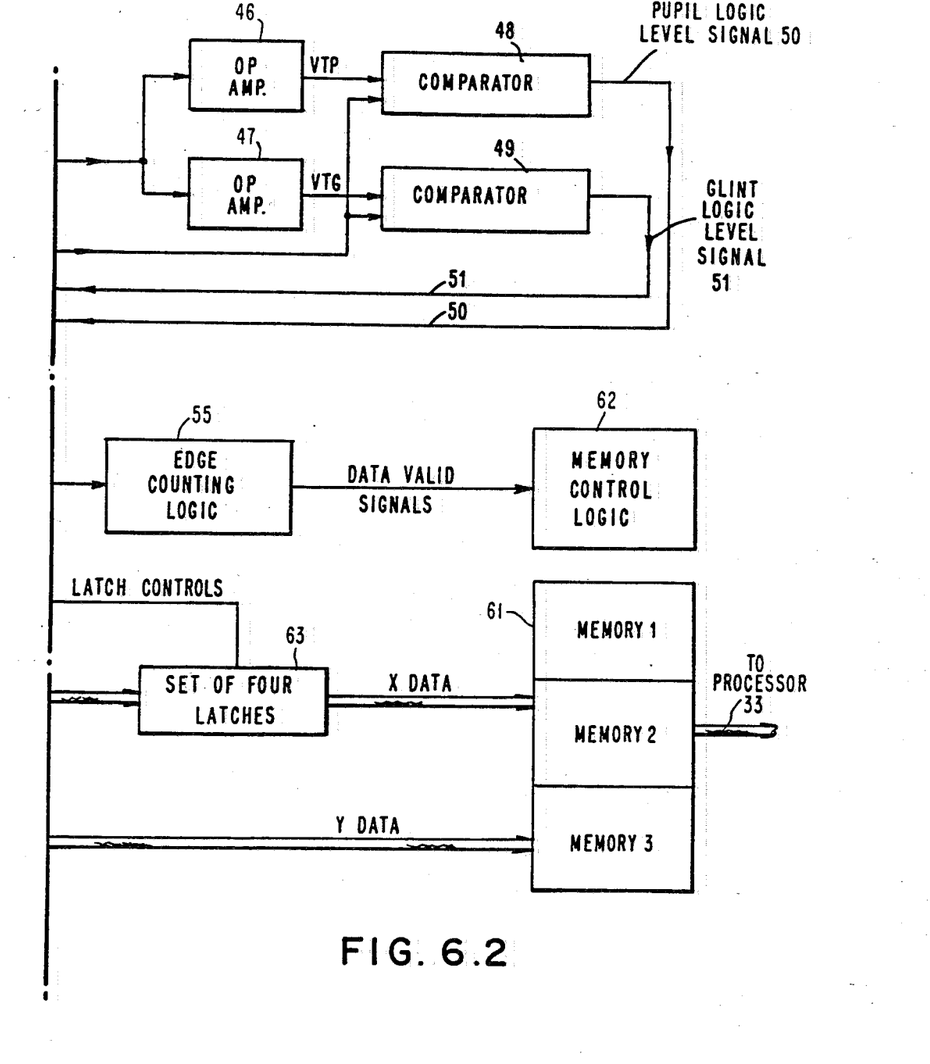
Figure 111:
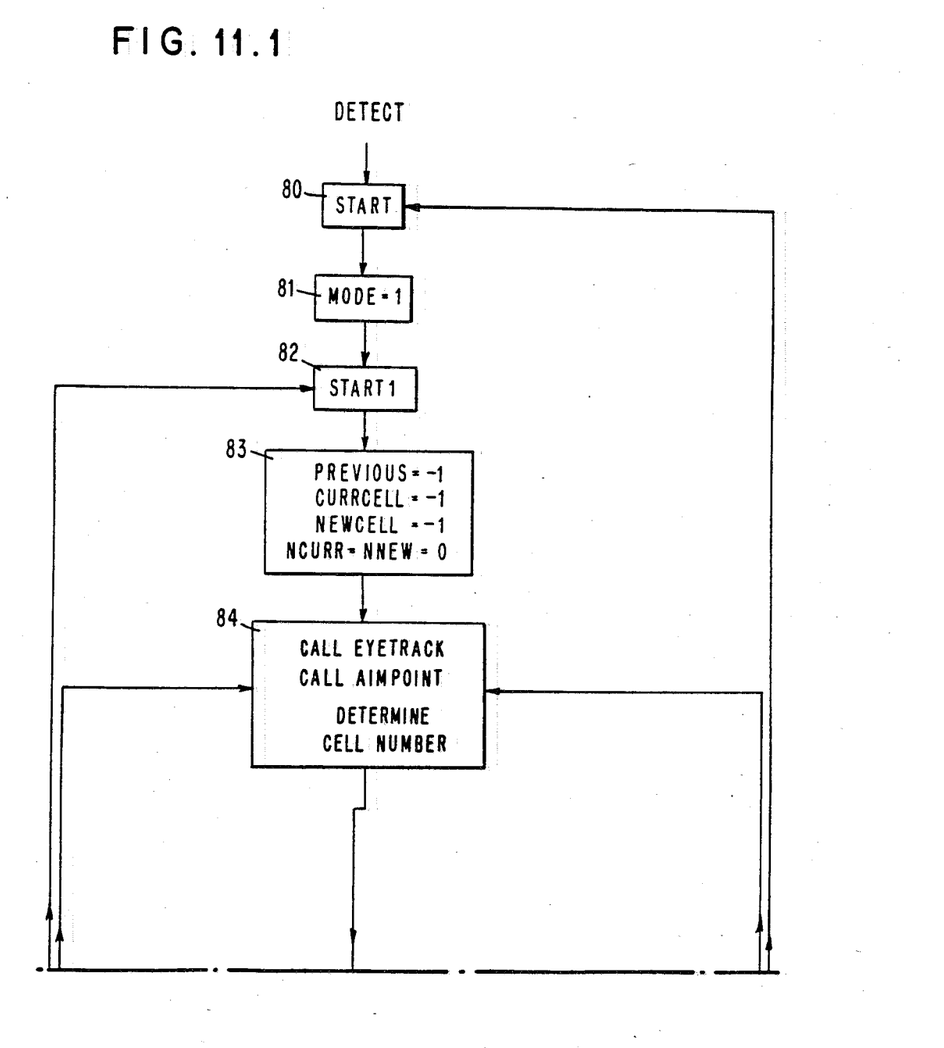
Figure 112:
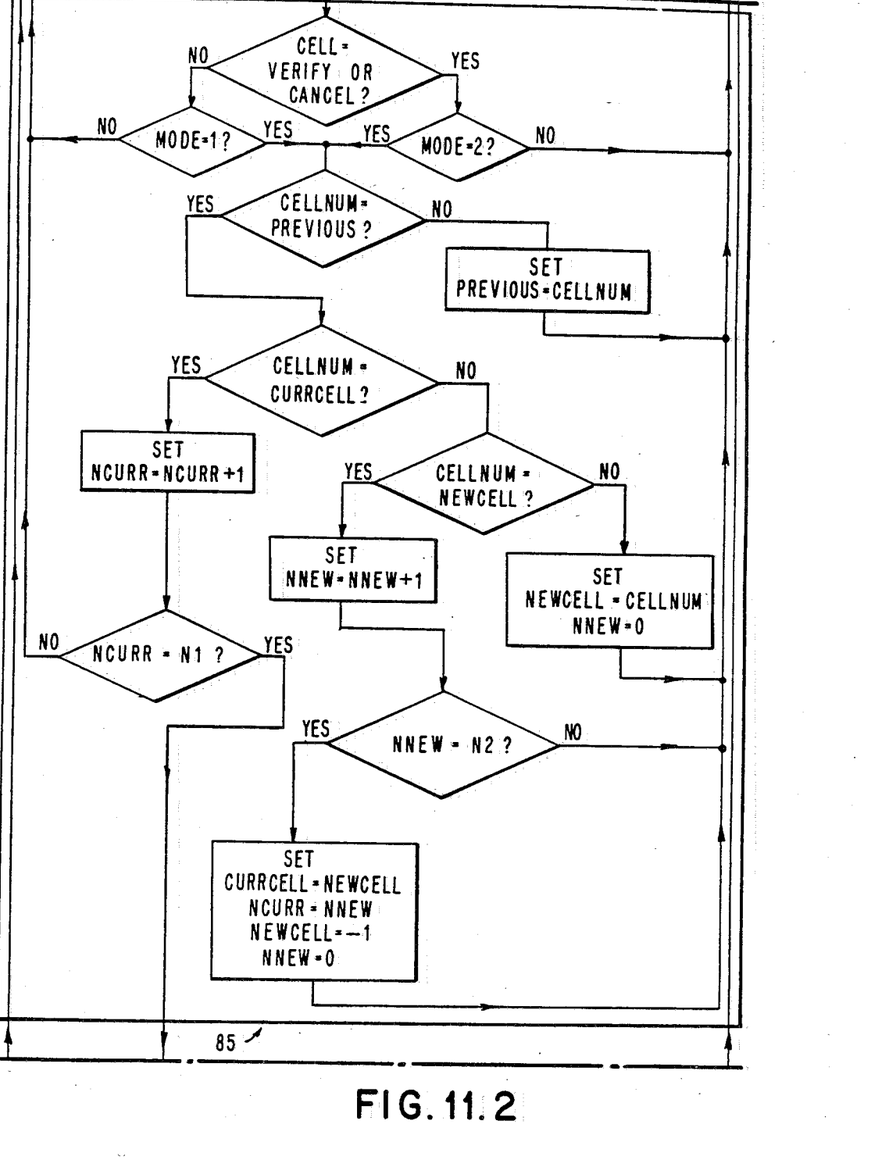
Figure 113:
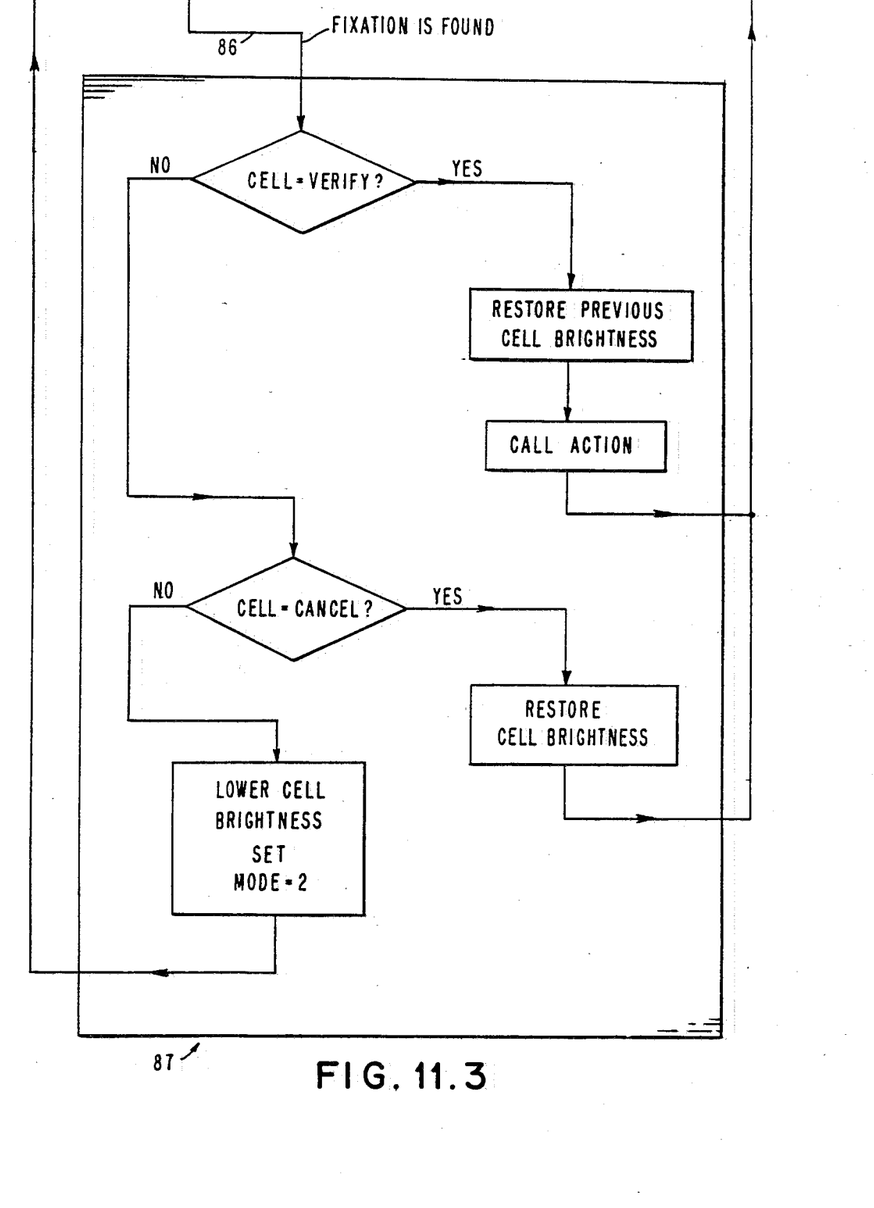

Having established in the DETECT subroutine of FIG. 11 a selection of a viewing area so as to convey information, the apparatus in response then performs an execution of an action. There are a variety of actions that can take place. For example, in the illustration where a book is being read, if the cell number upon which there is gaze fixation is assigned NEXT PAGE, the action would be to call from storage the contents of the next page and display it in the appropriate section of the display area replacing the current page. A subroutine that would be run in the processor 33 is provided to do this in FIG. 12. Referring to FIG. 12, the DETECT subroutine of FIG. 11 in section 87, calls this action subroutine and passes the cell number on which the fixation took place.

In the illustration of FIG. 12 a simplified illustrative operation is shown for the reading of a book. Most of the viewing area will be assigned as part of the reading material display area and there will be three regions labelled CELLS 1, 2 and 3 assigned the controls: STOP, NEXT PAGE and LAST PAGE, respectively. The subroutine is entered at START 110 and in section 111 the CELL number 1 is tested. If found, the operation terminates in section 112. If the CELL number tested in section 113 is 2, a display routine is called in section 114 which replaces the display with the next page, and if the cell is not 2, the display routine is called in section 115 and displays the previous page. After each such display, control returns to the DETECT program.

In accordance with the invention, a man-machine communicator is set forth wherein a combination of eye position information and partitioning of the viewing area into discrete locations with assignment of at least certain locations to-user-to-machine communication operates to provide an interactive level of communication.

An embodiment has been set forth wherein eye position information is determined optoelectronically with the axis of vision focus determined by reflected light along the same path as the source beam and user selection information obtained from a process of making an assumption followed by user verification.

The embodiment is set forth employing both analog and digital type computations but it will be apparent to one skilled in the art in the light of the principles set forth that many tradeoffs are possible in structural assemblies and computation methods.

Having thus described our invention, what we claim as new, and desire to secure by Letters Patent is:

1. In a user-machine visual communication device of the type involving displayed data wherein a user indicates by the location of the gaze of said user on a partitioned display a proposed machine action and said machine executes said action based on a verificatin from said user of a displayed indication of that proposed action, the improvement comprising:

means for said machine to indicate a proposed interpretation of said user gaze movement derived from the parameters of gaze location points, time and frequency of occurrence by locally changing the intensity of a portion of said displayed data, and means for detecting in a specific location of said displayed data assigned for a verification signal concerning the information conveyed by said locally changing the intensity of a portion of said displayed data, the presence of the gaze location of said user.

* * * * *